US009788993B2

(12) United States Patent
Yoshimura et al.

(10) Patent No.: US 9,788,993 B2
(45) Date of Patent: Oct. 17, 2017

(54) MOUTH CAP FOR LIQUID CONTAINER

(75) Inventors: Seiji Yoshimura, Osaka (JP); Hirokazu Mihashi, Osaka (JP); Yorihisa Uetake, Aichi (JP)

(73) Assignees: Taisei Kako Co., Ltd., Osaka (JP); Nihon Tengantaku Kenkyusyo Co., Ltd., Aichi (JP)

( * ) Notice: Subject to any disclaimer, the term of this patent is extended or adjusted under 35 U.S.C. 154(b) by 453 days.

(21) Appl. No.: 14/397,948

(22) PCT Filed: May 9, 2012

(86) PCT No.: PCT/JP2012/061847
§ 371 (c)(1),
(2), (4) Date: Apr. 8, 2015

(87) PCT Pub. No.: WO2013/168244
PCT Pub. Date: Nov. 14, 2013

(65) Prior Publication Data
US 2015/0216723 A1    Aug. 6, 2015

(51) Int. Cl.
A61F 9/00 (2006.01)
B65D 47/18 (2006.01)
B65D 47/20 (2006.01)
B65D 47/24 (2006.01)
(Continued)

(52) U.S. Cl.
CPC ............ *A61F 9/0008* (2013.01); *B65D 47/18* (2013.01); *B65D 47/2031* (2013.01); *B65D 47/2075* (2013.01); *B65D 47/2093* (2013.01); *B65D 47/247* (2013.01); *B65D 47/0804* (2013.01); *B65D 47/128* (2013.01)

(58) Field of Classification Search
CPC . A61F 9/0008; B65D 47/0804; B65D 47/128; B65D 47/18; B65D 47/2031; B65D 47/2075; B65D 47/2093; B65D 47/247
See application file for complete search history.

(56) References Cited

U.S. PATENT DOCUMENTS 9,422,100 B2 *   8/2016  Uetake ................. B65D 47/18
2003/0230596 A1 * 12/2003  Masuda ................ B65D 35/14
                                              222/92

FOREIGN PATENT DOCUMENTS

DE   102007019507 A1   10/2008
WO      0222458 A1     3/2002
(Continued)

OTHER PUBLICATIONS

International Search Report dated Jul. 24, 2012.

*Primary Examiner* — Tatyana Zalukaeva
*Assistant Examiner* — Benjamin Klein
(74) *Attorney, Agent, or Firm* — Wood, Phillips, Katz, Clark & Mortimer

(57) ABSTRACT

A plug member integrally includes a base portion (35a) attached to a plug holder (31) to be mounted on a mouth portion of a container, a plug (34) engaged with an engagement portion (31c) provided in an outlet passage of the plug holder (31), and a resilient connection portion (35b) resiliently connecting the plug (34) to the base portion (35a). Before the first use, the outlet passage is closed with the plug member. In the first use, the container is squeezed to increase the internal pressure of the container. Thus, the plug (34) is disengaged from the engagement portion (31c) by the internal pressure. The outlet passage is thereafter constantly kept open.

2 Claims, 13 Drawing Sheets

(51) Int. Cl.
*B65D 47/08* (2006.01)
*B65D 47/12* (2006.01)

(56) References Cited

FOREIGN PATENT DOCUMENTS

| | | |
|---|---|---|
| WO | 2005118152 A1 | 12/2005 |
| WO | 2009147952 A1 | 12/2009 |

* cited by examiner

MOUTH CAP FOR LIQUID CONTAINER

TECHNICAL FIELD

The present invention relates to a mouth cap for a liquid container.

BACKGROUND ART

The applicants of the present invention disclose prior-art filtering discharge containers each employing a delaminatable bottle (delaminatable laminate bottle) to be advantageously used for aseptic eyedropper containers, for example, in the following PLT1 and PLT2.

CITATION LIST

Patent Literature

PLT1: JP-2002-80055-A
PLT2: JP-2009-179403-A

These prior-art filtering discharge containers each include an outer layer bottle having a squeeze-deformable body and a mouth portion provided at an upper end of the body, an inner layer bag provided in the outer layer bottle and having an opening connected to the mouth portion of the outer layer bottle, and a mouth cap attached to the mouth portion of the outer layer bottle. The outer layer bottle has an inlet hole through which outer air is introduced between the outer layer bottle and the inner layer bag. The mouth cap has an outlet passage through which a content liquid contained in the inner layer bag is discharged from the inner layer bag, and a filter and a check valve are provided in the outlet passage.

The filter is a membrane filter or the like which has a multiplicity of minute pores and prevents passage of virus and bacteria. In PLT1, the check valve principally includes a valve body resiliently supported by a thin piece. In PLT2, the check valve principally includes a valve body made of a resilient material and having a cross-shaped orifice formed in a valve head of the valve body.

SUMMARY OF INVENTION

Technical Problem

The multiplicity of minute pores of the filter are closed with water in a so-called air-locked state when being wetted. In this state, air cannot pass through the filter, unless a pressure higher than a bubble point of the filter is applied to the filter. Therefore, the filter is maintained in a dry state during the storage of the container before the first use.

However, a highly osmotic medicinal liquid is liable to leak from the check valve of the prior-art container mouth cap mechanism to wet the filter, which is in turn air-locked. Therefore, air remaining on the upstream side of the filter after the first use problematically prevents the discharge of the content liquid. In the check valve disclosed in PLT1, a valve hole is closed with a disk-shaped valve body in abutment against the valve hole. Therefore, a relatively small contact force is present between the valve body and the valve hole, so that the highly osmotic medicinal liquid is likely to leak from between the valve body and the valve hole. In the check valve disclosed in PLT2, the orifice is defined by an incision, and no external force acts on the orifice to firmly close the orifice, so that the highly osmotic medicinal liquid is likely to leak from the orifice.

In the check valve mechanism, the valve body is provided for drawing the medicinal liquid from the downstream side of the filter. When the content liquid is dispensed dropwise in the second and subsequent use, it is necessary to lift the valve head to open the orifice. Therefore, the outer layer bottle should be relatively heavily squeeze-deformed against the lifting resistance to dispense the content liquid dropwise. This makes it impossible to provide a comfortable use feeling.

Besides the prior-art delaminatable containers, there are single layer bottles for a variety of cosmetics and detergents. An outlet of such a single layer bottle is sealed with a seal member such as a pull-ring or an aluminum seal film, which is removed by a user before use. However, this arrangement requires a sealing member removing operation, which is troublesome for some users.

It is therefore an object of the present invention to provide a mouth cap structure, which is applicable to various liquid containers, reliably prevents the content liquid from leaking to the filter before the first use, facilitates an unplugging operation to be performed through a simple content liquid discharging operation by a user in the first use, and has a reduced discharging resistance in the second and subsequent use.

Solution to Problem

To achieve the object described above, the present invention has the following technical aspects:

According to the present invention, there is provided a liquid container mouth cap, which includes: a plug holder to be attached to a mouth portion of a liquid container and having an outlet passage through which a content liquid is discharged; and a plug provided in the outlet passage. The plug holder includes an engagement portion provided in the outlet passage thereof, the plug engaged with the engagement portion so as to close the outlet passage and to be allowed to pop out from the engagement portion by an increased internal pressure of the liquid container.

In the liquid container mouth cap according to the present invention, the plug is engaged with the engagement portion to close the outlet passage. When the plug is not engaged with the engagement portion, the outlet passage is defined around the plug for discharging the content liquid. The plug is engaged with the engagement portion with an engagement force sufficient to prevent the leakage of the content liquid until the first discharging operation. Thus, the leakage of the content liquid is reliably prevented. Although the mouth cap is configured such that the plug is engaged with the engagement portion, the plug can be disengaged from the engagement portion by an internal pressure of the container increased by squeeze-deforming the container body. This obviates the need for performing a special unplugging operation when the content liquid is discharged for the first time, but it is simply necessary to relatively heavily squeeze the container body only in the first discharging operation. When the plug is disengaged from the engagement portion, the plug is liable to be instantaneously popped out from the engagement portion by the internal pressure of the pressurized container. This results in plosive vibrations. Even if the state of the plug cannot be visually checked from the outside, the user can recognize the communication of the outlet passage based on the vibrations. The mouth cap is configured such that, with the plug holder mounted on the mouth portion, the plug cannot be removed from the plug holder. Therefore, the plug is prevented from escaping from the plug holder to the outside when the plug is disengaged from the engagement portion.

According to the present invention, there is provided another liquid container mouth cap, which includes a plug holder attached to a mouth portion of a liquid container and having an outlet passage through which a content liquid is discharged, and a plug member retained in the plug holder. The plug member integrally includes: a base portion attached to the plug holder; a plug provided in the outlet passage; and a resilient connection portion resiliently connecting the plug to the base portion. The plug holder includes an engagement portion provided in the outlet passage thereof. The plug is engaged with the engagement portion with a predetermined force, the resilient connection portion applies an urging force for urging the plug downstream, the urging force being smaller than the engagement force, and the engagement force and the urging force generated by pushing the plug upstream after attaching the base portion to the plug holder.

In the liquid container mouth cap according to the present invention, the plug is engaged with the engagement portion to close the outlet passage. When the plug is not engaged with the engagement portion, the outlet passage is defined around the plug for discharging the content liquid. The plug is engaged with the engagement portion with an engagement force sufficient to prevent the leakage of the content liquid until the first discharging operation. Thus, the leakage of the content liquid is reliably prevented. Although the mouth cap is configured such that the plug is engaged with the engagement portion, the plug can be disengaged from the engagement portion by an internal pressure of the container increased by squeeze-deforming the container body. This obviates the need for performing a special unplugging operation when the content liquid is discharged for the first time, but it is simply necessary to relatively heavily squeeze the container body only in the first discharging operation. At this time, an urging force accumulated in the resilient connection portion facilitates the disengagement of the plug from the engagement portion. This makes it possible to reduce an operation force required for the first discharging operation, while providing the engagement force sufficient for the prevention of the leakage of the content liquid. After the plug is disengaged from the engagement portion in the first discharging operation, the plug is maintained in a disengaged position by the resilient connection portion to be thereby prevented from being re-engaged with the engagement portion to close the outlet passage. Thus, the content liquid can be smoothly discharged with a relatively small force in the second and subsequent discharging operation. Since the plug, the base portion and the resilient connection portion are unified as a plug member, it is possible to facilitate the assembling operation and to reduce the number of the components and the production costs. Further, the mounting position of the plug is determined by the mounting position of the base portion. Therefore, the plug is automatically positioned with respect to the engagement portion, thereby reducing the possibility of an engagement failure in the mass production. When the plug is disengaged from the engagement portion, the plug is liable to be instantaneously popped out from the engagement portion by the internal pressure of the pressurized container. This results in plosive vibrations. Even if the state of the plug cannot be visually checked from the outside, the user can recognize the communication of the outlet passage based on the vibrations. The mouth cap is configured such that, with the plug holder attached to the mouth portion, the plug cannot be removed from the plug holder. Therefore, the plug is prevented from escaping from the plug holder to the outside when the plug is disengaged from the engagement portion.

The mouth cap according to the present invention further includes a cover attached to the plug holder. The plug holder has an attachment recess provided on a downstream end thereof for accommodating the plug member. The base portion is fitted in the recess, and the engagement portion is disposed in an inner side of the attachment recess. The cover has a top portion covering the attachment recess, and includes an outlet nozzle portion provided in the top portion. The cover is attached to the plug holder with the base portion and the plug of the plug member being respectively combined with the attachment recess and the engagement portion. This facilitates the plug member combining operation, and makes it possible to reliably engage the plug with the engagement portion by pressing the plug against the engagement portion from above. Further, the plug holder and the cover are combined together to be handled as a single attachment component. Therefore, the mouth cap (attachment component) can be attached to the container mouth portion after a content liquid filling operation is performed in a content liquid filling plant. This improves the mass productivity and the quality control.

DESCRIPTION OF EMBODIMENTS

Preferred embodiments of the present invention will hereinafter be described with reference to the drawings.

Figure 1:
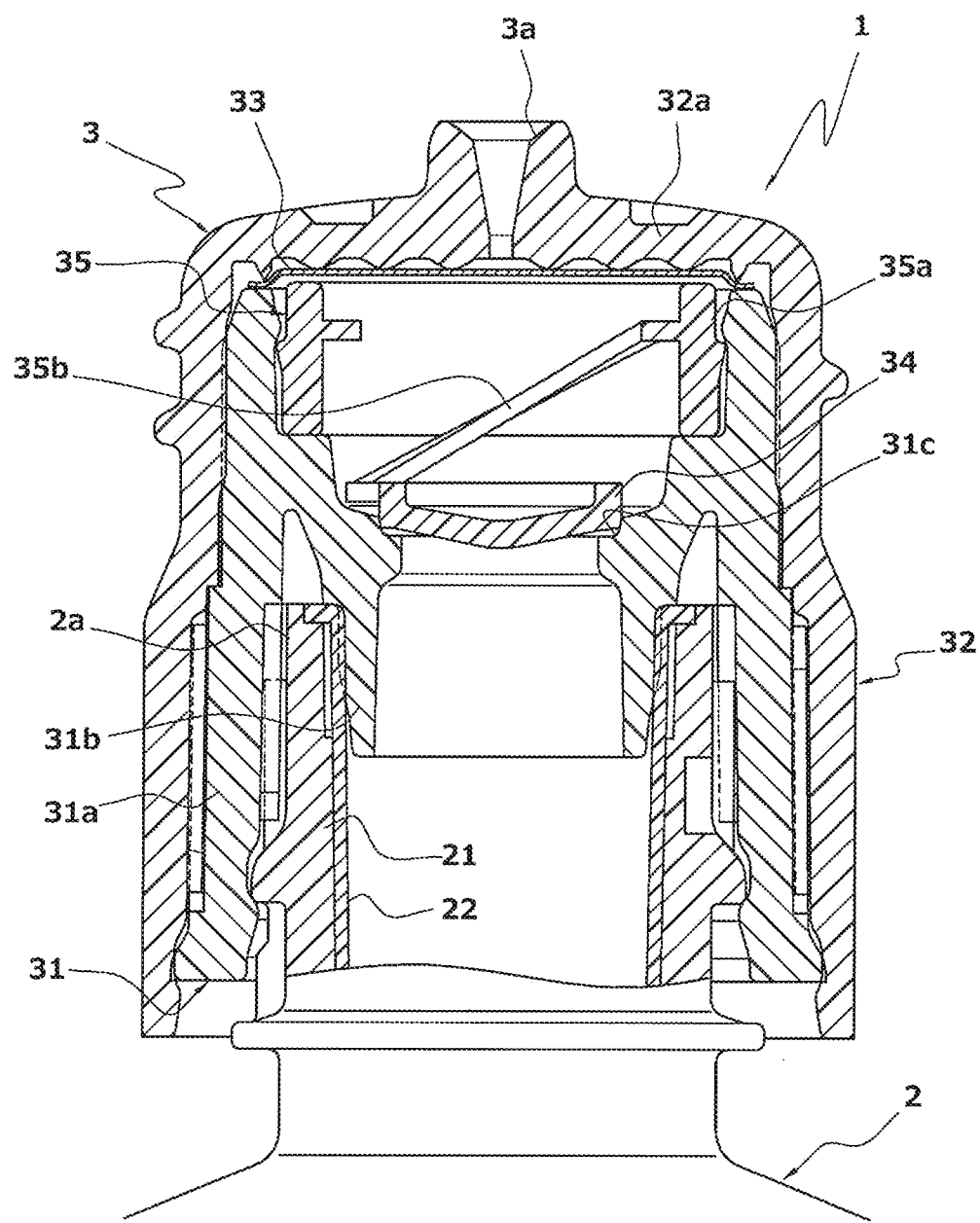
FIG. 1 is a sectional view showing a major portion of an eyedropper container including a mouth cap according to a first embodiment of the present invention in a sealed state.
Figure 2:
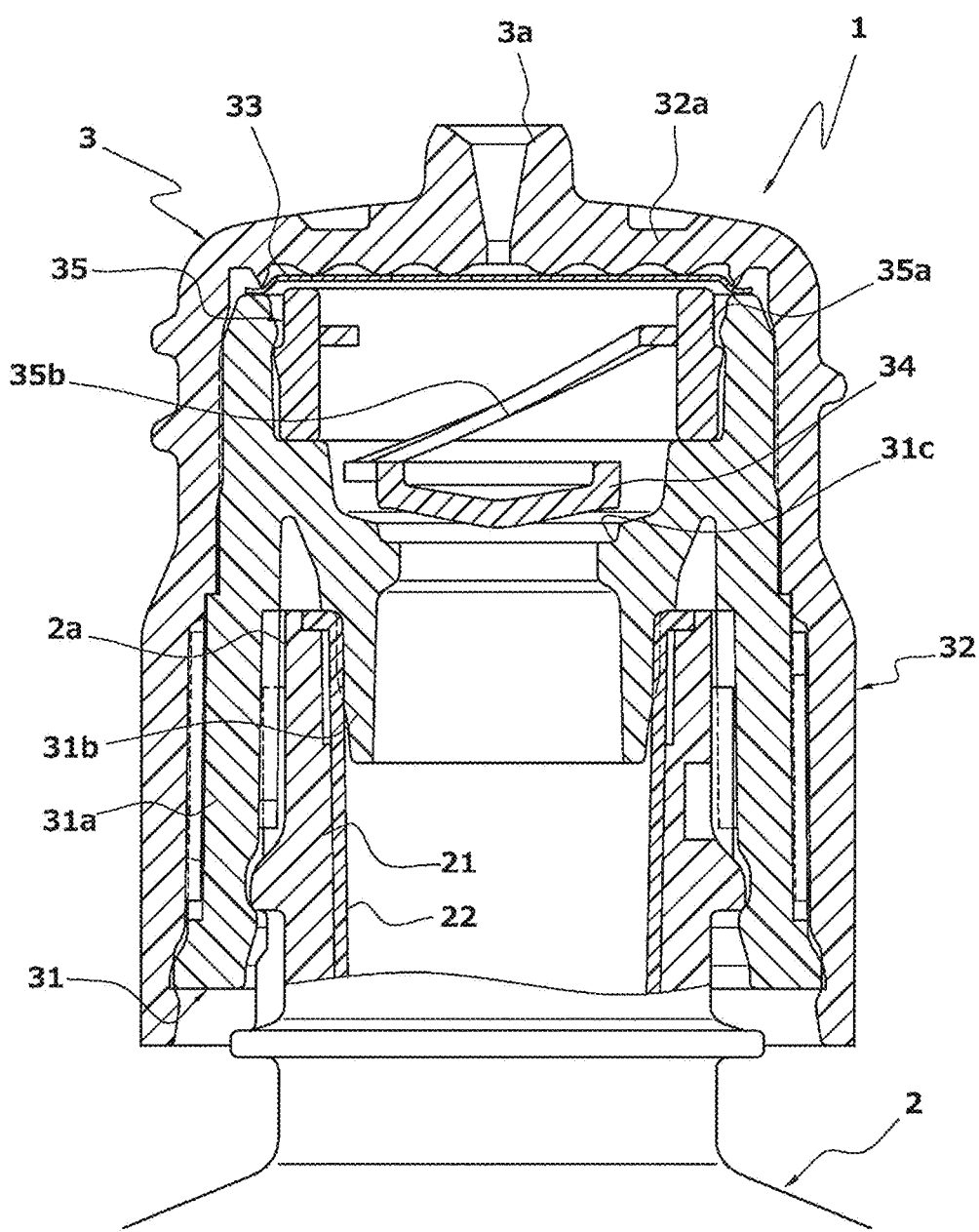
FIG. 2 is a sectional view showing the major portion of the container in an unsealed state.

FIGS. 1 and 2 illustrate an eyedropper container 1 including a liquid container mouth cap structure according to a first embodiment of the present invention. The eyedropper container 1 has the same basic construction as disclosed in PLT1 and PLT2. The eyedropper container 1 includes a laminate bottle 2 having a double layer structure including an inner layer and an outer layer produced by blow-molding a bottomed tubular laminate parison, and a mouth cap 3 attached to a mouth portion 2*a* of the bottle 2. The mouth cap 3 has an outlet passage through which a content medicinal liquid is discharged. A filter 33 and a plug 34 for closing the outlet passage on an upstream side of the filter 33 with respect to a discharging direction until the first discharging operation are provided in the outlet passage of the mouth cap 3. The content medicinal liquid (fluid) contained in the bottle 2 flows through the outlet passage in the mouth cap 3 to be dispensed dropwise from a distal nozzle portion 3*a* by inverting the laminate bottle 2 and press-squeezing the body of the laminate bottle 2.

The laminate bottle 2 has a layered structure including an outer layer bottle 21 (squeeze bottle) defining the outer layer and an inner layer bag 22 (fluid containing bag) defining the inner layer. The outer layer bottle 21 and the inner layer bag 22 each have a hollow cylindrical mouth portion and a body having an oval cross section immediately after the blow molding. The outer layer bottle 21 is formed from a synthetic resin such as PET or SBS, and the inner layer bag 22 is formed from a synthetic resin (e.g., a polyolefin such as a polypropylene or a polyethylene) easily delaminatable from the outer layer bottle 21 and preferably withstanding electron beam sterilization and γ-ray sterilization. The mouth portion of the bag 22 serves as an opening through which the content medicinal liquid is discharged, and the opening of the bag 22 is fixedly connected to the mouth portion of the outer layer bottle 21.

The outer layer bottle 21 is configured such that an upper edge of a resiliently squeeze-deformable bottomed tubular body thereof is connected to the hollow cylindrical mouth portion via a shoulder having a diameter progressively reduced in an upward direction. The outer layer bottle 21 may have any configuration, and may have rigid front and back walls as disclosed in PLT2. The outer layer bottle 21 has an inlet hole (not shown) through which outer air is introduced between the outer layer bottle 21 and the inner layer bag 22. The inlet hole is preferably provided in the body of the outer layer bottle 21 as disclosed in PLT2, but may be provided in the bottom or the mouth portion of the bottle.

The body of the inner layer bag 22 has a film shape, and is easily deformable to be shrunk as the amount of the content medicinal liquid decreases. Further, the inner layer bag 22 has restoration resilience such that the content medicinal liquid remaining in the distal nozzle portion 3*a* of the outlet passage on a downstream side of the filter 33 with respect to the discharging direction after the discharge of the content medicinal liquid can be sucked back to the upstream side of the filter 33. On the other hand, the mouth portion of the inner layer bag 22 has a greater thickness than the body of the inner layer bag 22.

The mouth cap 3 includes a hollow cylindrical plug holder 31, a cover 32 fitted around the plug holder 31, and the filter 33 and the plug 34 described above. The outlet passage for the content medicinal liquid extends vertically through a center portion of the plug holder 31. The cover 32 has a disk-shaped top portion 32*a* (top plate), and the nozzle portion 3*a* extends vertically through the center of the top portion. The outlet passage through which the content medicinal liquid contained in the inner layer bag 22 is discharged is defined by the nozzle portion 3*a* and the center outlet passage of the plug holder 31. The top portion may entirely have a nozzle shape.

The plug holder 31 includes a tubular base portion 31*a* fitted around the mouth portion of the outer layer bottle 21, and a tubular content liquid outlet portion 31*b* provided integrally in the base portion 31*a* and having a smaller diameter than the base portion 31*a*. The content liquid outlet portion 31*b* is liquid-tightly fitted in the bottle mouth portion 2*a*. The content liquid outlet portion 31*b* has a plug engagement recess 31*c* (engagement portion) provided along an upper edge thereof as opening upward. An inner peripheral surface of the plug holder 31 has a diameter that is increased progressively or stepwise in an upward direction from the engagement portion 31*c*. A resilient support member 35 of the plug 34 is accommodated in an attachment recess (inner space) provided along an upper edge (downstream edge) of the plug holder 31.

The cover 32 is fitted around the plug holder 31 from above to be thereby combined with the plug holder 31. Before the combining, the filter 33 is provided on the lower side of the top portion 32*a*. The distal nozzle portion 3*a* of the mouth cap 3 is disposed at the center of the cover 32. The content medicinal liquid passing through the filter 33 is discharged from the distal nozzle portion 3*a* to the outside.

Usable as the filter 33 are a membrane filter, a sintered filter, a hydrophilic porous planar filter, a hydrophobic porous planar filter and the like which can prevent pathogenic bacteria and virus from passing through the filter 33 from the downstream side of the filter 33 (the outside of the container) to the upstream side of the filter 33 (the inside of the container) with respect to the discharging direction. The filter 33 is disposed on a downstream side of the plug 34 with respect to the discharging direction, and the outer peripheral edge of the filter is melt-bonded to the upper edge of the plug holder 31.

The plug 34 has a disk shape having a center portion slightly bulged downward, and is liquid-tightly engaged with the engagement portion 31*c*. In this embodiment, the plug 34 is squeezed into the engagement portion 31*c* from above, whereby an engagement force sufficient to prevent the plug 34 from being disengaged from the engagement portion 31*c* due to a slight increase in the internal pressure of the bottle or vibrations occurring during the storage or transportation of the bottle is generated between the plug 34 and the engagement portion 31*c*. In this embodiment, the plug 34 and the resilient support member 35 which supports the plug 34 are integrally molded to serve as a single plug member. The resilient support member 35 urges the plug 34 engaged with the engagement portion 31 upward (away from the engagement portion 31*c*) and, after the plug 34 is disengaged upward from the engagement portion 31*c*, supports the plug 34 in a disengaged position, i.e., supports the plug 34 in a position upwardly apart from the engagement portion 31*c*. An urging force to be applied by the support member 35 is smaller than the engagement force.

Figure 3:
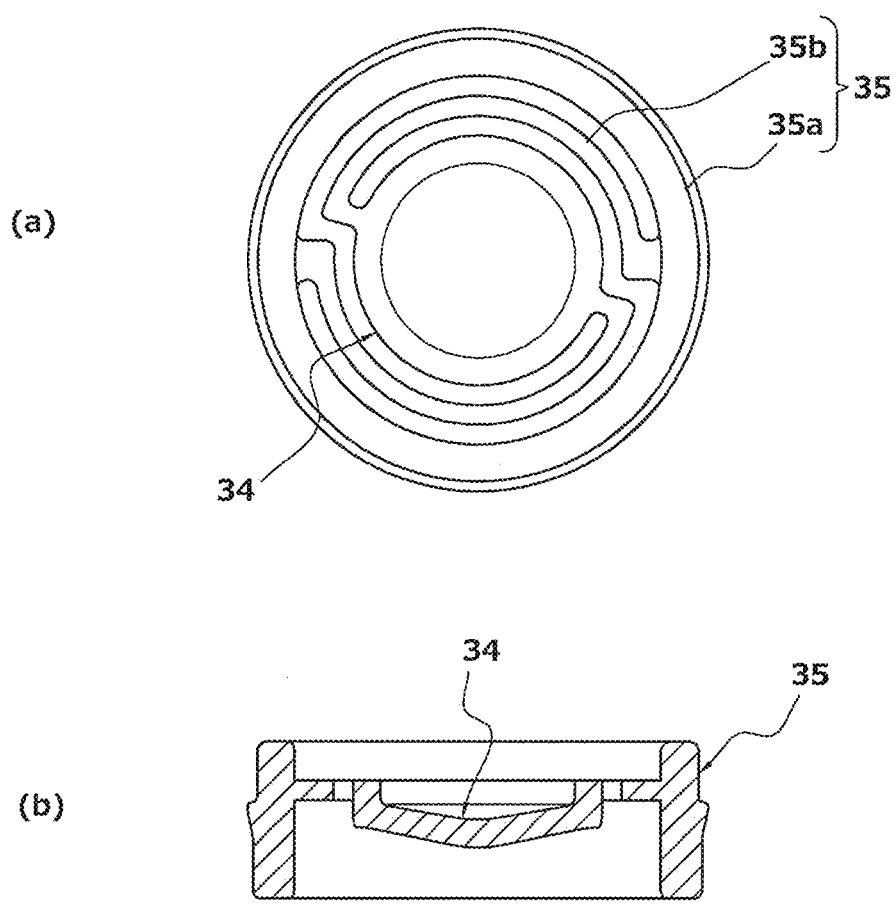
FIGS. 3(a) and 3(b) are a plan view and a vertical sectional view, respectively, showing a plug member of the container.

More specifically, as shown in FIG. 3, the plug member including the resilient support member 35 and the plug 34 is an elastic member molded from a polyethylene, a polypropylene or an elastomer with the use of a metallocene catalyst. The resilient support member 35 includes a hollow cylindrical base portion 35*a* and a pair of arcuate resilient connection portions 35*b* which are integrally molded. The base portion 35*a* is fitted in an upper end attachment recess of the plug holder 31, and the resilient connection portions 35*b* are provided on front and rear sides to connect the base portion 35*a* to the plug 34. The outer diameter of the plug 34 is smaller than the inner diameter of the base portion 35a, so that the content medicinal liquid uniformly flowing out from around the plug 34 disengaged from the engagement portion 31c flows through an inner peripheral portion of the base portion 35a toward the filter 33. The number of the resilient connection portions 35b is not particularly limited. The number or the strength of the resilient connection portions 35b may be such that the plug 34 can be maintained in the position apart from the engagement portion 31c.

In the eyedropper container 1 according to this embodiment, the plug 34 is engaged with the engagement portion 31c as shown in FIG. 1 before the first discharging operation, whereby the outlet passage in the mouth cap 3 is reliably closed. Even if the content medicinal liquid is highly osmotic, the content medicinal liquid can be reliably prevented from leaking from the plug 34 to the downstream side. This prevents the air-lock which may otherwise occur when the filter 33 is wetted.

In the first discharging operation, the container 1 is inverted, and then the bottle body is squeeze-deformed with the inlet hole being closed with a finger or the like. Thus, the internal pressure of the inner layer bag 22 is increased, whereby the plug 34 is pushed up from the engagement portion 31c by the internal pressure as shown in FIG. 2. At this time, the push-up force of the plug 34 is enhanced by the resilient connection portions 35b, so that the first discharging operation can be smoothly performed. In the first discharging operation, the air present between the filter 33 and the plug 34 is expelled through the dry filter 33 by the content liquid. Thereafter, the space under the filter 33 is filled with the content medicinal liquid. Thus, the filter 33 is constantly wetted with the content medicinal liquid.

In the second and subsequent discharging operation, the inside of the inner layer bag 22 constantly communicates with the filter 33, so that the squeeze force to be applied to the bottle body for the discharging is reduced. Thus, the discharging operation can be smoothly performed. Since the outer air cannot pass through the wetted filter, there is no possibility that the outer air is introduced to the upstream side of the filter in the second and subsequent discharging operation. This prevents a discharging failure which may otherwise occur due to the air lock. Further, the medicinal liquid remaining on the downstream side of the filter 33, i.e., the medicinal liquid remaining in the outlet nozzle portion 3a, is sucked back to the upstream side of the filter 33 by the restorability of the inner layer bag 22, thereby preventing the proliferation of bacteria in the nozzle portion 3a.

Figure 4:
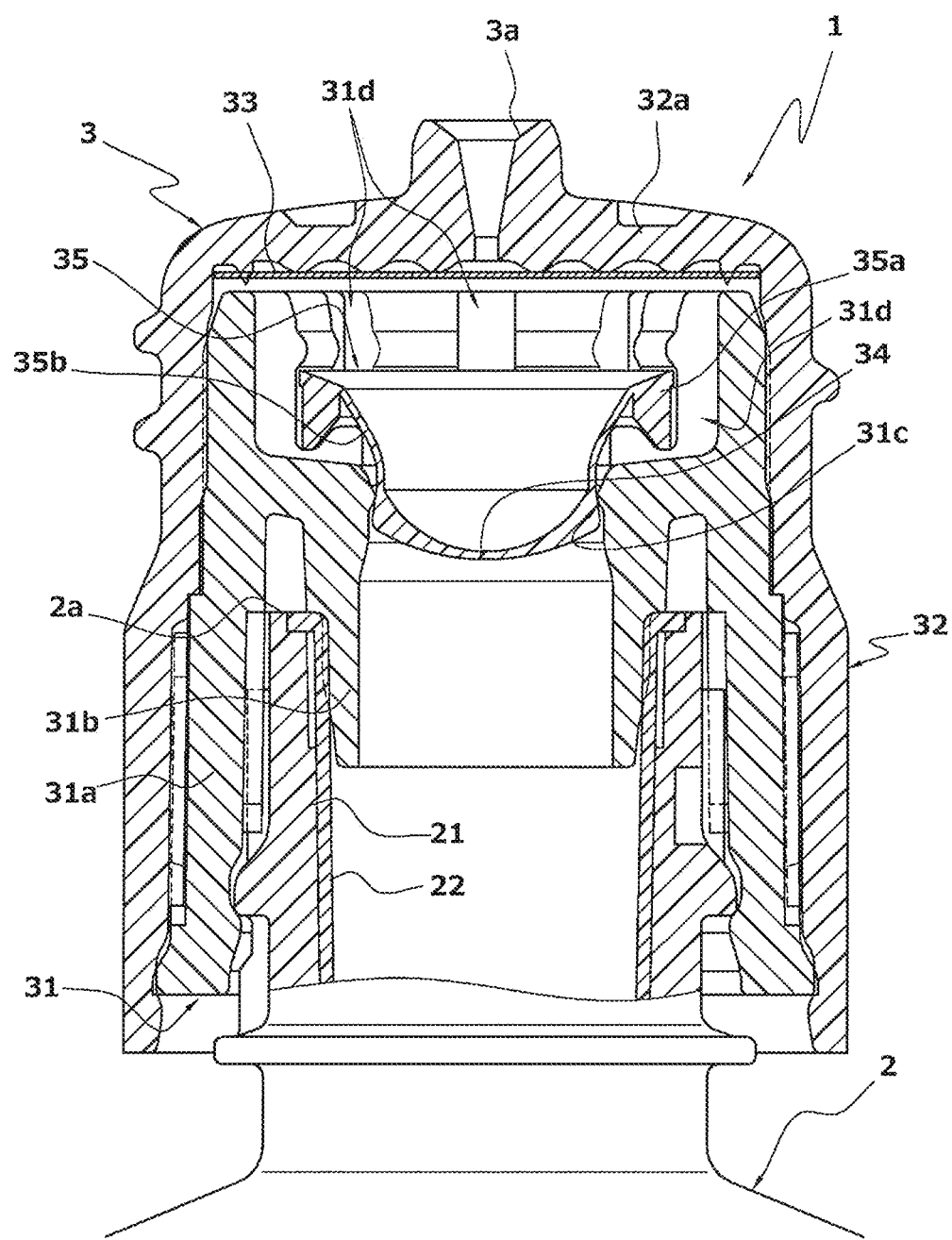
FIG. 4 is a sectional view showing a major portion of an eyedropper container including a mouth cap according to a second embodiment of the present invention in a sealed state.
Figure 5:
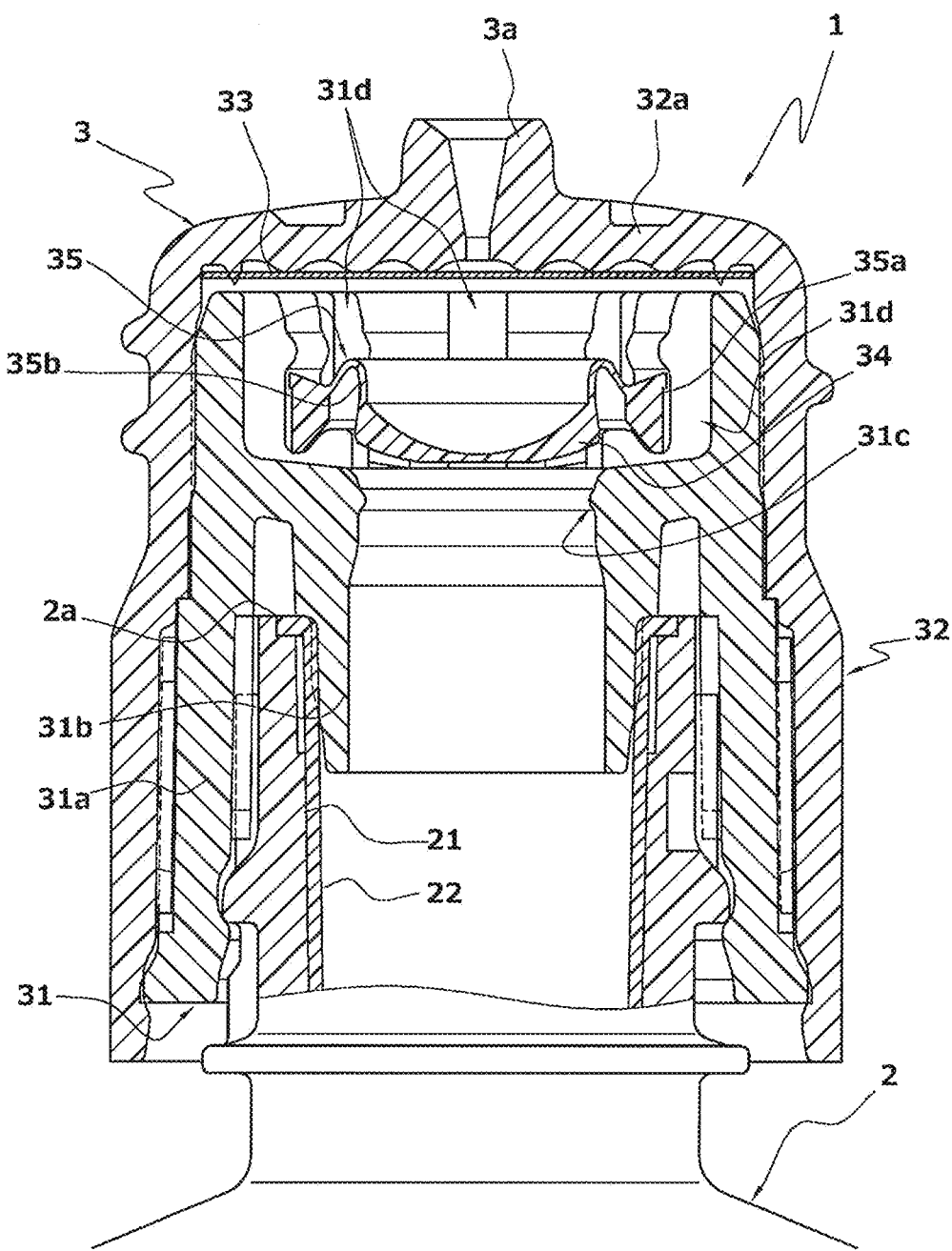
FIG. 5 is a sectional view showing the major portion of the container in an unsealed state.
Figure 6:
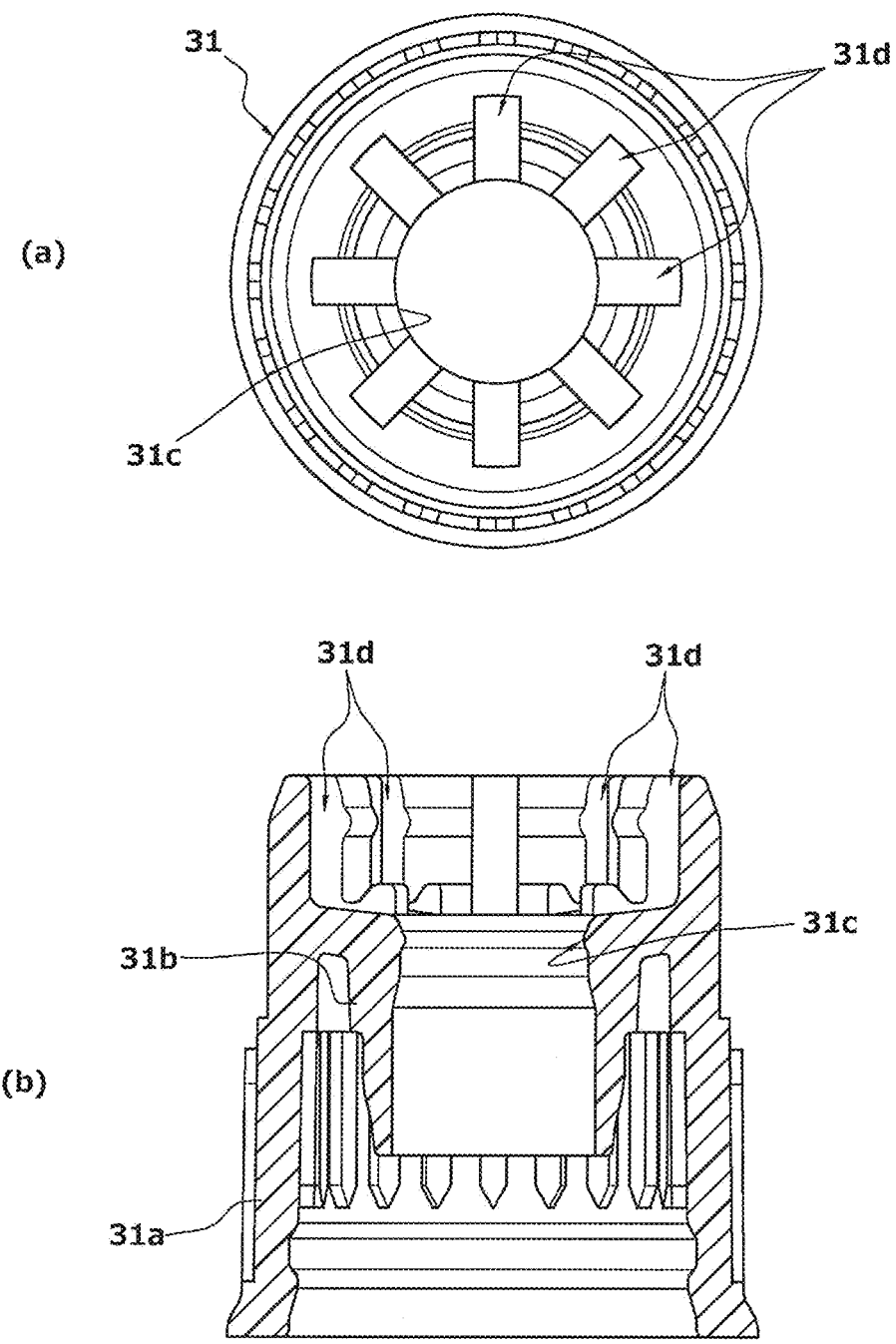
FIGS. 6(a) and 6(b) are a plan view and a vertical sectional view, respectively, showing a plug holder of the container.

FIGS. 4 to 6 illustrate a filtering discharge container 1 according to a second embodiment of the present invention. Components corresponding to those in the first embodiment are designated by the same reference characters as in the first embodiment, and will not be described in detail. Therefore, different components and different functions and effects will be described.

In this embodiment, the plug 34 is formed from an elastic material such as a silicone rubber, a chlorinated butyl rubber or an elastomer. A plug flange 35a (base portion) and a connector sleeve 35b (resilient connection portion) constituting the resilient support member 35, and a plug head 34 constituting the plug 34 are integrally molded. The plug flange 35a has a generally ring shape, and has a generally triangular section having a thickness increased toward radially outward. The connector sleeve 35b has a generally hollow cylindrical shape. The connector sleeve 35b is integrally connected at one of axially opposite ends thereof to an inner peripheral edge of the plug flange 35a, and integrally connected at the other axial end thereof to the outer peripheral edge of the plug head 34. The connector sleeve 35b has a relatively thin and flexible structure for easy deformation and, as shown in FIG. 4, has a restoration resilience with respect to an axially shrinking direction when being axially elongated. The initial shape of the connector sleeve 35b is shown in FIG. 5. Of course, the plug head 34 is not formed with the cross-shaped orifice disclosed in PLT2.

Further, an upper end portion of a content liquid outlet portion 31b of a valve holder 31 has an inner surface having a diameter progressively reduced in an upward direction, and a minimum diameter portion of the content liquid outlet portion 31b defines an engagement hole 31c (engagement portion). The plug head 34 is liquid-tightly fitted in the engagement hole 31c from above. As shown in FIG. 6, at least one or more communication channels 31d are provided in circumferential positions on an inner peripheral surface of the valve holder 31 above the engagement hole 31c, so that the content medicinal liquid can flow out from outer peripheries of the plug head and the plug flange toward the filter 33 with the plug head 34 being located upwardly apart from the engagement hole 31c. In FIG. 6, eight communication channels 31d are circumferentially equidistantly arranged, so that the content medicinal liquid can uniformly flow out from the entire circumference of the plug head 34. The communication channels 31d each have an L-shaped vertical section.

In this embodiment, lower inner surface portions of side walls of the L-shaped communication channels 31d are configured so as to be engaged with or lock the plug head 34 pushed up by the content liquid in order to more reliably support the plug head 34 apart from the engagement hole 31c. With this arrangement, the plug head 34 is reliably supported in a position upwardly apart from the engagement hole 31c. Of course, the plug head 34 may be supported in the position upwardly apart from the engagement hole 31c only by the resilient restoration force of the connector sleeve 35b.

In the container 1 according to this embodiment, as shown in FIG. 4, the plug head (plug) 34 is engaged with the engagement portion 31c to reliably prevent the content medicinal liquid from leaking before the first discharging operation. In the second and subsequent discharging operation, as shown in FIG. 5, the plug head 34 is supported in the disengaged position, whereby the content liquid can be discharged with a smaller squeeze force.

Figure 9:
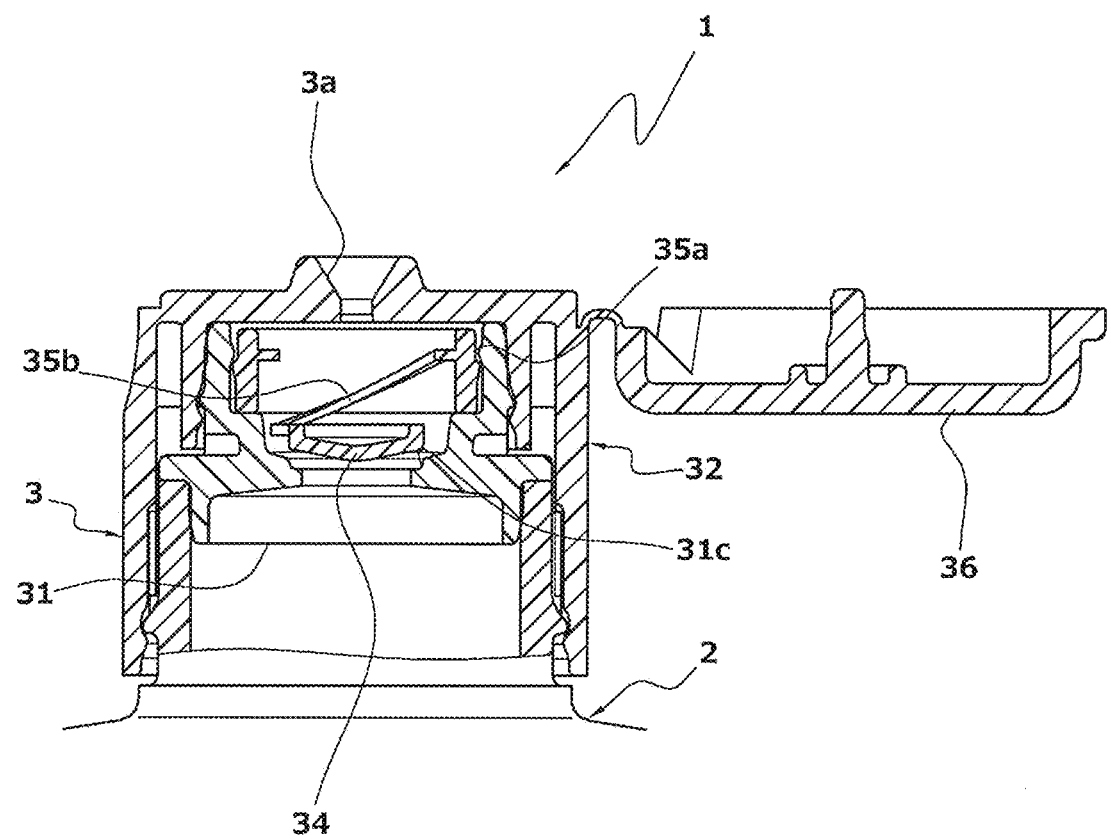
FIG. 9 is a sectional view showing the major portion of the container in a content liquid discharging operation.
Figure 10:
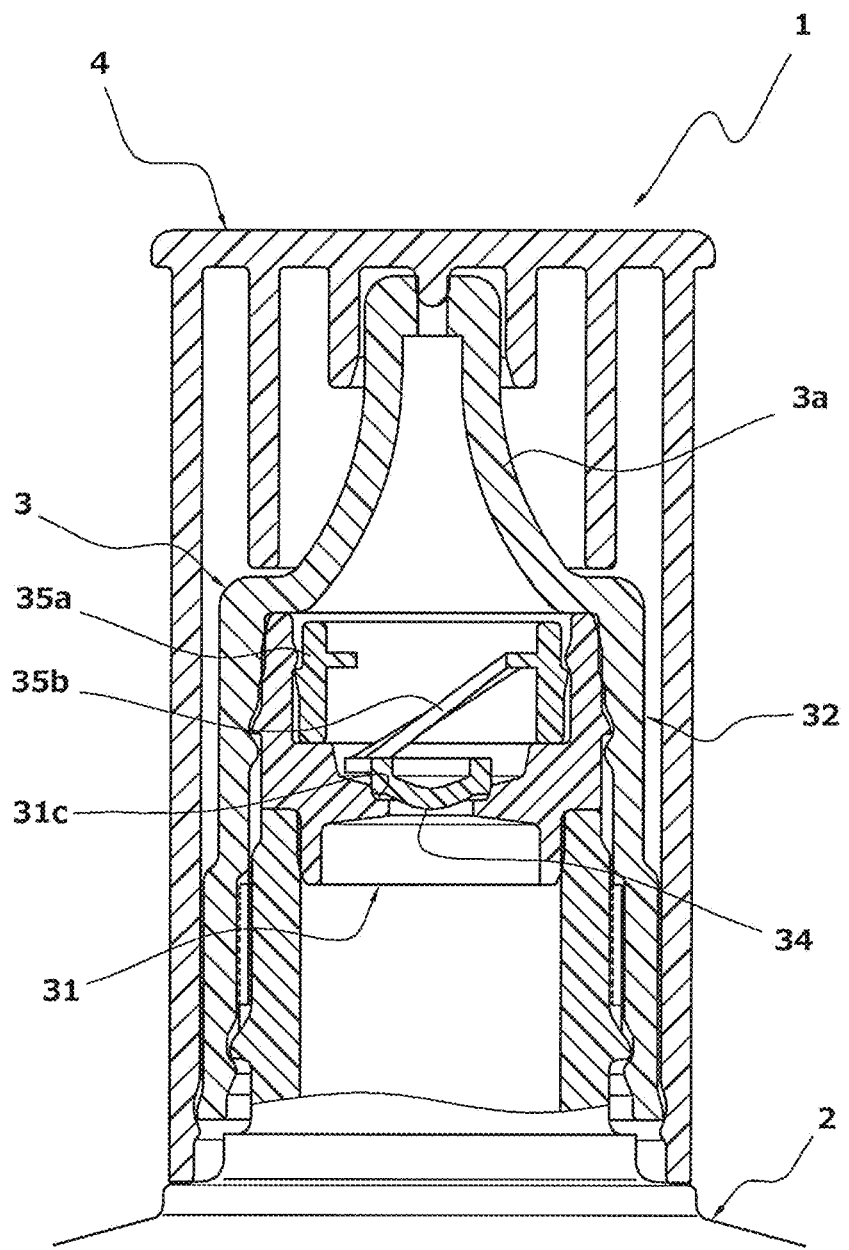
FIG. 10 is a sectional view showing a major portion of a liquid container including a mouth cap according to a fourth embodiment of the present invention in a sealed state.
Figure 11:
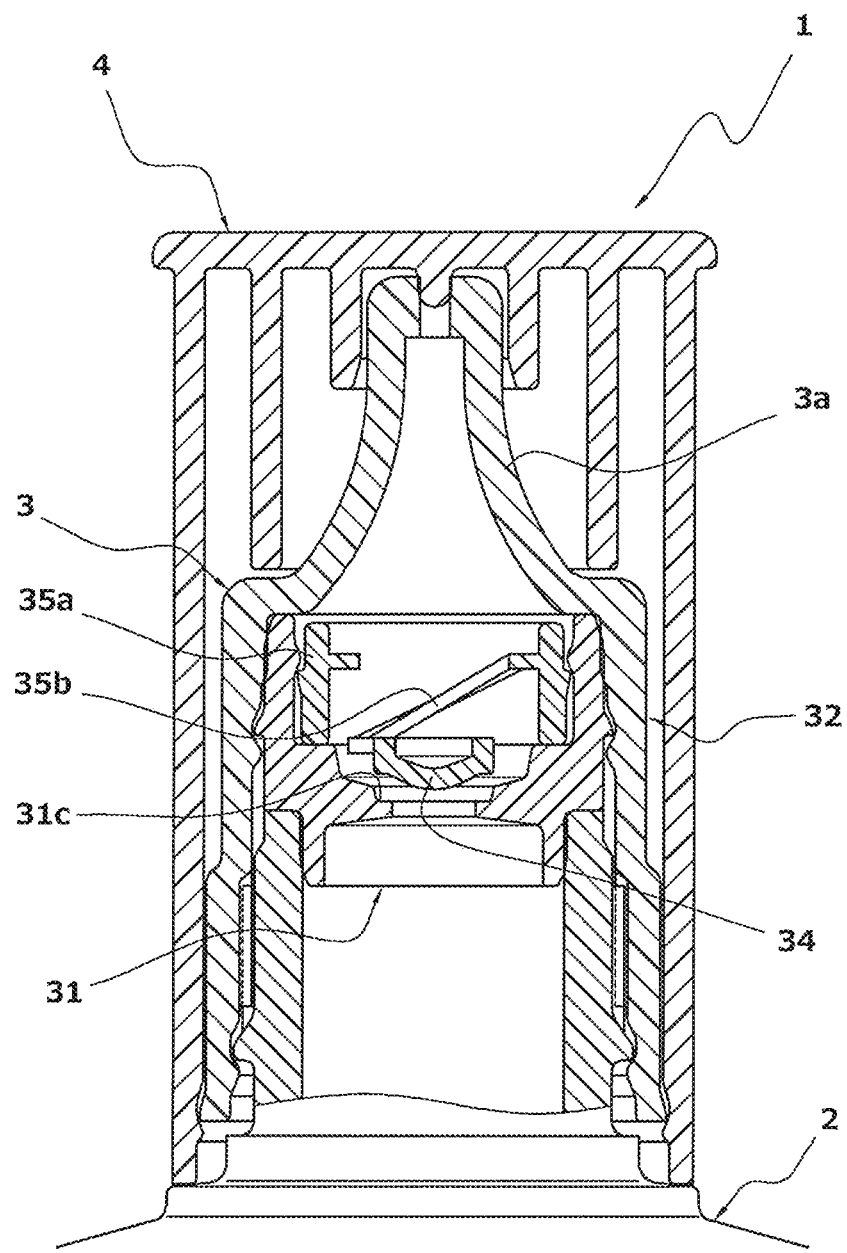
FIG. 11 is a sectional view showing the major portion of the container in an unsealing operation.
Figure 12:
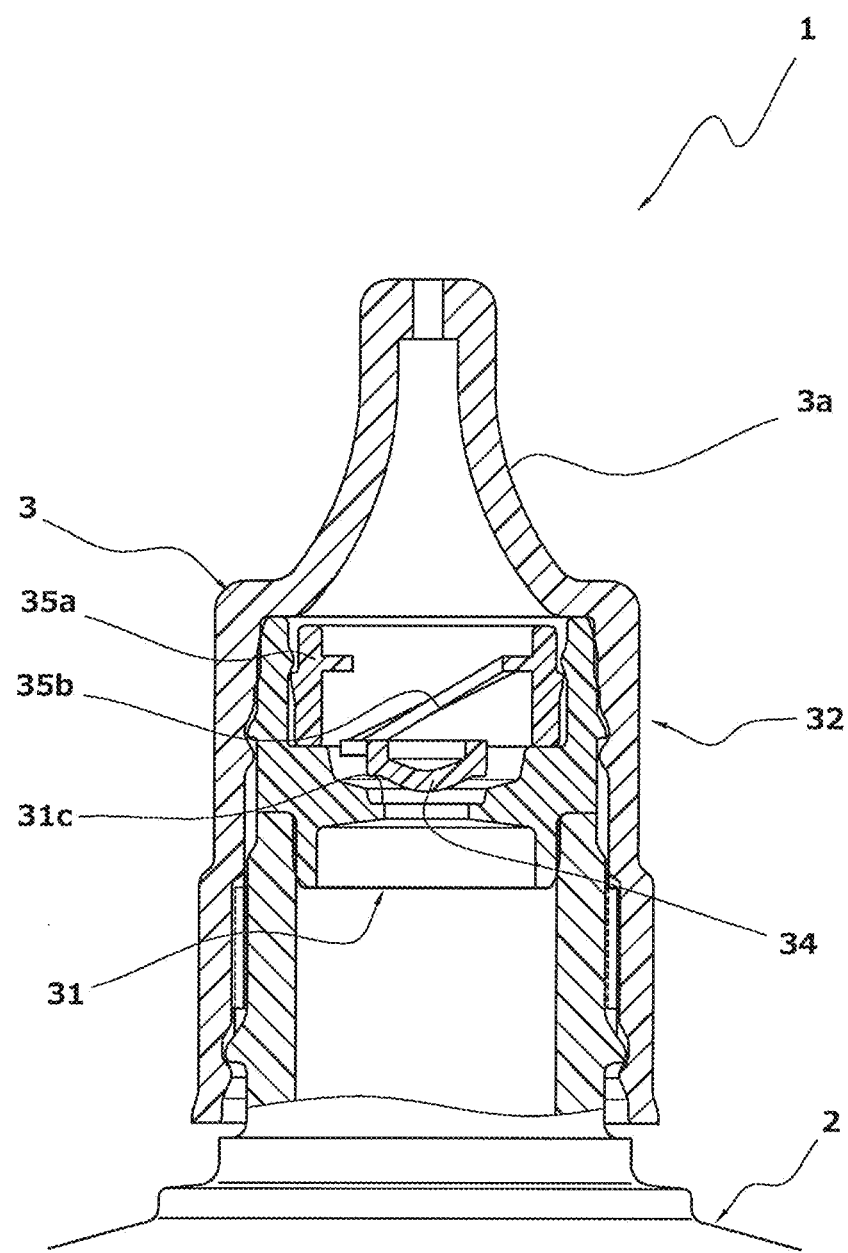
FIG. 12 is a sectional view showing the major portion of the container in a content liquid discharging operation.

The present invention is not limited to the aforementioned embodiments, but design modifications may be made as required. For example, the plug may be a spherical member without the provision of the base portion and the resilient connection portion. The present invention is applicable to a variety of dispenser containers and discharge containers other than the eyedropper container. A third embodiment shown in FIGS. 7 to 9 and a fourth embodiment shown in FIGS. 10 to 12 are advantageously applicable to mouth cap structures for liquid containers for cosmetics such as shampoos and hair conditioners. In these embodiments, container bottles 2 each have a single layer structure, and do not include the filter employed in the first and second embodiments. In these embodiments, components corresponding to those in the first and second embodiments will be designated by the same reference characters as in the first and second embodiments, and will not be described in detail. Therefore, different components and different functions and effects will be described.

Figure 7:
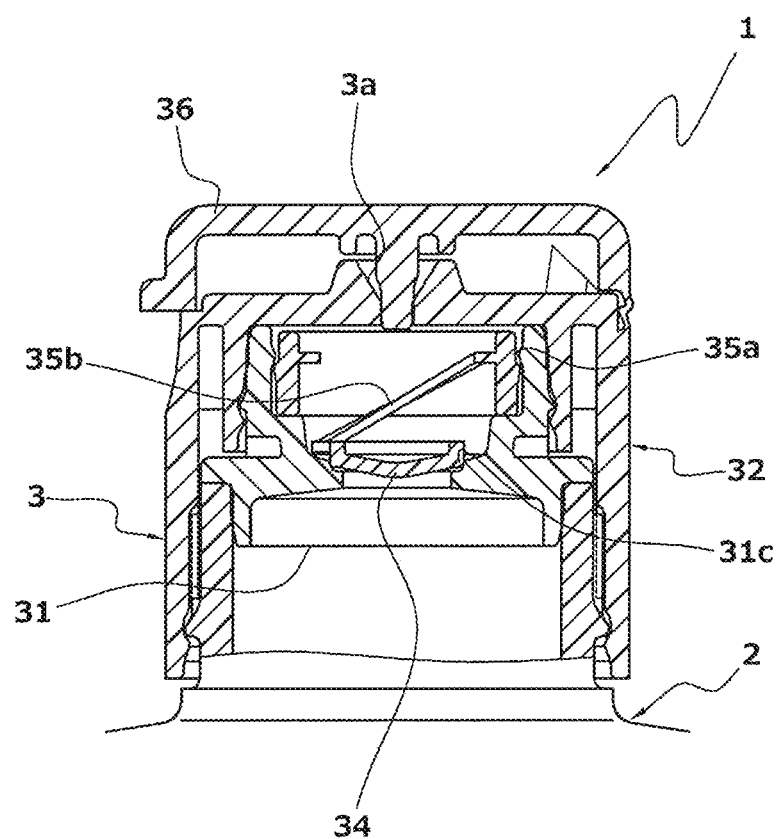
FIG. 7 is a sectional view showing a major portion of a liquid container including a mouth cap according to a third embodiment of the present invention in a sealed state.
Figure 8:
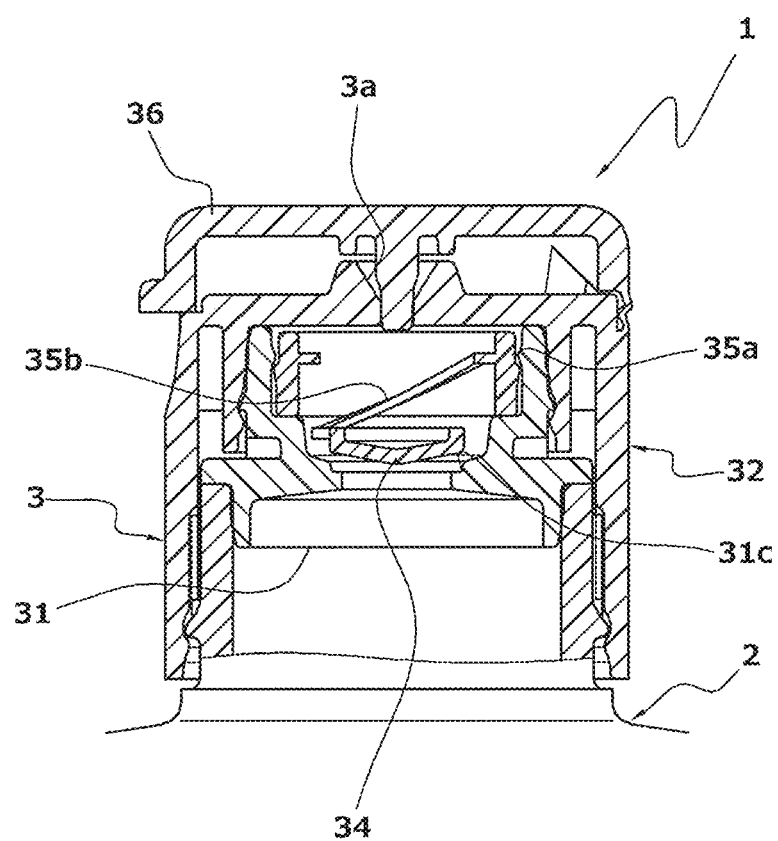
FIG. 8 is a sectional view showing the major portion of the container in an unsealing operation.

The mouth cap structure according to the third embodiment includes an openable hinged cap 36 provided on the top of the cover 32. With the hinged cap 36 closed, the outlet nozzle portion 3a is closed. However, the hinged cap 36 cannot reliably close the outlet nozzle portion 3a. Therefore, it is a conventional practice to shrink-package the outer periphery of the hinged cap or to seal the mouth portion of the container with an aluminum packaging material, which is removed by a user before use. In this embodiment, as shown in FIG. 7, the outlet passage can be reliably sealed with the plug 34 in the mouth cap 3 before use. Prior to the start of the use, as shown in FIG. 8, the bottle body is squeezed to increase the internal pressure of the container to disengage the plug 34 from the engagement portion 31c. Thus, the outlet passage in the mouth cap 3 is constantly open, so that the content liquid can be thereafter used simply by opening and closing the hinged cap 33.

In the mouth cap structure according to the fourth embodiment, the top portion of the cover 32 is entirely defined as the outlet nozzle portion 3a, and a cap 4 covering the outlet nozzle portion 3a is removably attached to the cover 32. The other arrangement is the same as in the third embodiment, and will not be described in detail.

Figure 13:
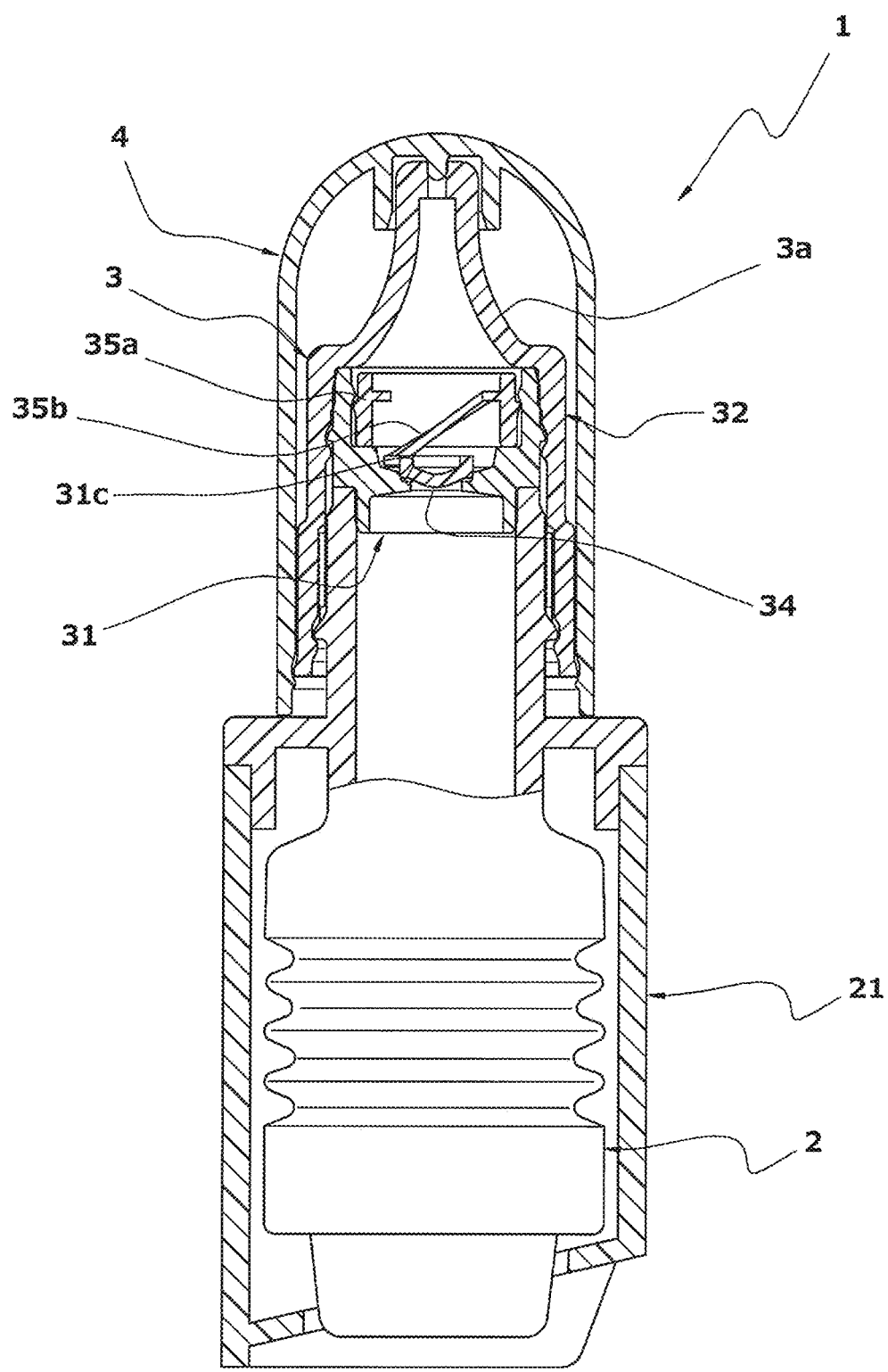
FIG. 13 is a whole sectional view of a liquid container according to a fifth embodiment of the present invention.

FIG. 13 illustrates an eyedropper container 1 according to a fifth embodiment of the present invention. Components corresponding to those in the fourth embodiment will be designated by the same reference characters as in the fourth embodiment, and will not be described in detail. Therefore, different components and different functions and effects will be described.

In the eyedropper container 1 according to the fifth embodiment, the bottle 2 has a bellows-shaped body which is axially deformable for expansion and contraction. The bottle 2 further has a cup-shaped bottom portion which has a smaller diameter than the bellows-shaped body. The outer periphery of the body of the bottle 2 is covered with a bottomed hollow cylindrical outer cover member 21. The bottom of the bottle 2 projects outward from an opening provided in a bottom plate of the outer cover member 21. The outer cover member 21 is removably attached to the bottle 2. When a greater compressive force is to be applied to the inside of the bottle 2 in order to disengage the plug 34 from the engagement portion 31c, the outer cover member 21 is removed from the bottle 2, so that the bellows-shaped bottle 2 can be significantly press-deformed. After the disengagement of the plug 34, on the other hand, the outer cover member 21 is attached to the bottle 2 with the bottle bottom portion projecting from the opening of the bottom plate of the outer cover member 21. By pushing the bottle bottom portion, a predetermined compressive force occurs in the bottle, whereby a predetermined amount of the content liquid can be stably dispensed dropwise.

REFERENCE SIGNS LIST

1 CONTAINER
2 BOTTLE
3 MOUTH CAP
3a OUTLET NOZZLE
3b SUPPORT PORTION
31 PLUG HOLDER
31c ENGAGEMENT PORTION
32 COVER
33 FILTER
34 PLUG
35 RESILIENT SUPPORT MEMBER

The invention claimed is:

1. A liquid container mouth cap, comprising:
a plug holder to be attached to a mouth portion of a liquid container and having an outlet passage through which a content liquid is discharged,
a plug provided in the outlet passage, and
a plug member retained in the plug holder,
wherein
the plug holder includes an engagement portion provided in the outlet passage thereof, the plug engaged with the engagement portion so as to close the outlet passage and to be allowed to pop out from the engagement portion by an increased internal pressure of the liquid container,
the plug member integrally includes a base portion attached to the plug holder, the plug provided in the outlet passage, and a resilient connection portion resiliently connecting the plug to the base portion, and
the plug is engaged with the engagement portion with a predetermined force, the resilient connection portion applies an urging force for urging the plug downstream, the urging force being smaller than the predetermined force, and the predetermined force and the urging force generated by pushing the plug upstream after attaching the base portion to the plug holder.

2. The liquid container mouth cap according to claim 1, further comprising a cover attached to the plug holder,
wherein the plug holder has an attachment recess provided on a downstream end thereof for accommodating the plug member,
wherein the base portion is fitted in the recess, and the engagement portion is disposed in an inner side of the attachment recess,
wherein the cover has a top portion covering the attachment recess, and includes an outlet nozzle portion provided in the top portion,
wherein the cover is attached to the plug holder with the base portion and the plug of the plug member being respectively combined with the attachment recess and the engagement portion.

* * * * *